US012629132B2

(12) United States Patent
Beers

(10) Patent No.: US 12,629,132 B2
(45) Date of Patent: May 19, 2026

(54) ULTRASOUND IMAGING PROBE WITH A TRANSDUCER ARRAY WITH A SHEAR-WAVE-MITIGATED COMPOUND LENS

(71) Applicant: GE Precision Healthcare LLC, Waukesha, WI (US)

(72) Inventor: Christopher Beers, State College, PA (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 158 days.

(21) Appl. No.: 18/744,892

(22) Filed: Jun. 17, 2024

(65) Prior Publication Data

US 2025/0380927 A1    Dec. 18, 2025

(51) Int. Cl.
*A61B 8/00* (2006.01)

(52) U.S. Cl.
CPC .......... *A61B 8/4444* (2013.01); *A61B 8/4488* (2013.01); *A61B 8/485* (2013.01)

(58) Field of Classification Search
CPC ...... A61B 8/4444; A61B 8/4488; A61B 8/485
See application file for complete search history.

(56) References Cited

U.S. PATENT DOCUMENTS

| 4,387,720 | A | 6/1983 | Miller |
| 5,577,507 | A | 11/1996 | Snyder et al. |
| 6,182,341 | B1 | 2/2001 | Talbot et al. |
| 7,888,847 | B2 | 2/2011 | Dietz et al. |
| 9,214,152 | B2 | 12/2015 | Kunkel et al. |
| 9,842,583 | B2 | 12/2017 | Kunkel et al. |
| 2016/0098984 | A1* | 4/2016 | Kunkel ................. A61B 8/4483 |
| | | | 367/137 |
| 2019/0257943 | A1* | 8/2019 | Beers .................... B06B 1/0292 |
| 2022/0202296 | A1 | 6/2022 | Zalev et al. |

FOREIGN PATENT DOCUMENTS

EP           337409581 B1      6/2023

* cited by examiner

*Primary Examiner* — Michael J Carey
*Assistant Examiner* — Zainab Mohammed Aldarraji
(74) *Attorney, Agent, or Firm* — Daugherty & Del Zoppo, Co. LPA

(57) ABSTRACT

An ultrasound imaging probe includes a backing layer, an acoustic stack with an interconnect coupled to the backing layer, a transducer array electrically coupled interconnect and including at least one transducer element with a transducing surface and at least one matching layer with a first side acoustically coupled to the transducing surface and a second opposing side, a compound lens including an inner lens with a planer inner side acoustically coupled to the second opposing side of the matching layer and a first non-flat side that is non-flat in elevation and wavy at least in azimuth and an outer lens with an outer side configured to contact a subject or object, and a second non-flat side that is non-flat in elevation and wavy at least in azimuth, wherein the first non-flat side of the inner lens is acoustically coupled to the second non-flat side of the outer lens.

20 Claims, 8 Drawing Sheets

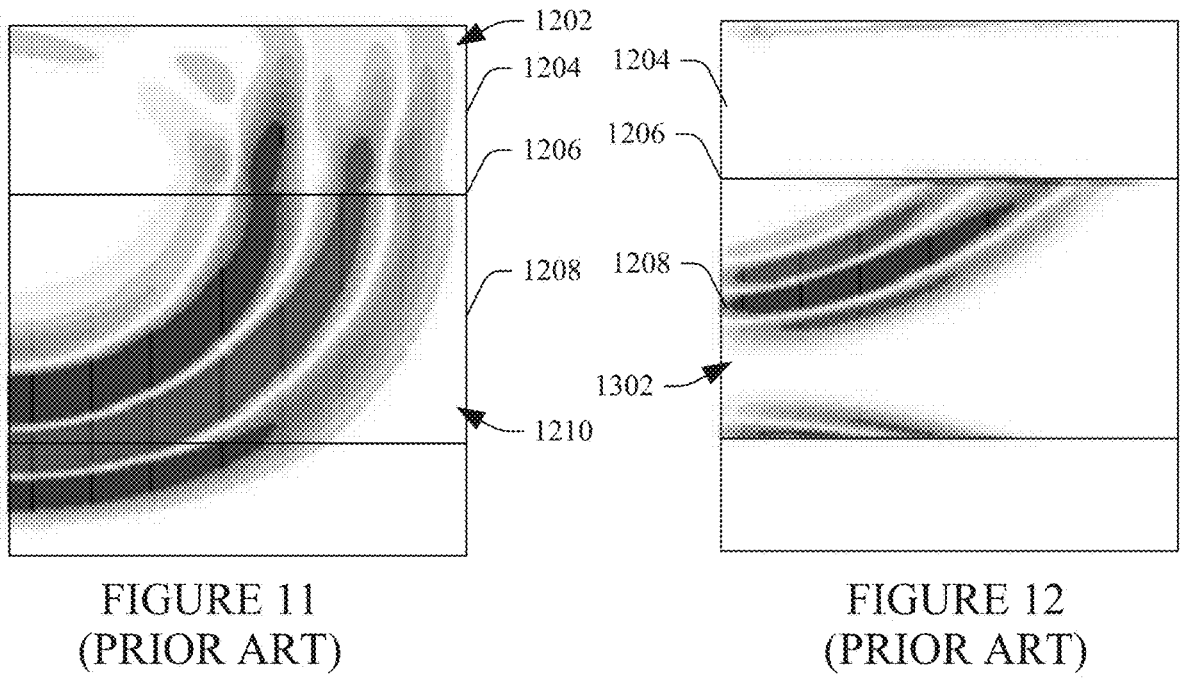
1202
1204
1206
1208
1210
1204
1206
1208
1302
FIGURE 11
(PRIOR ART)
FIGURE 12
(PRIOR ART)
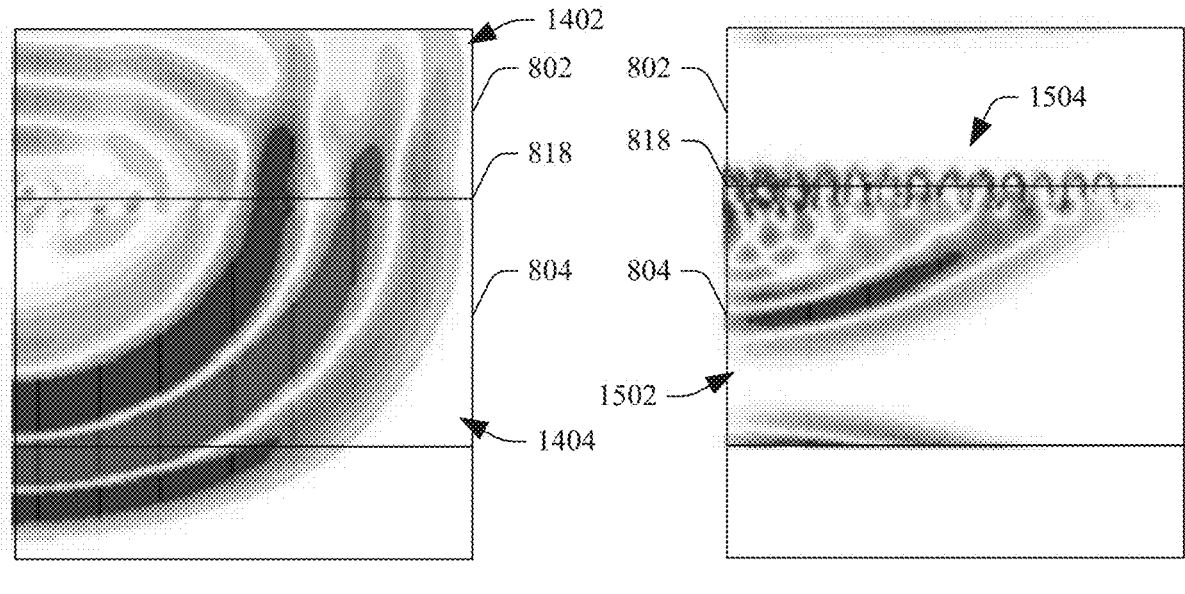
1402
802
818
804
1404
802
818
804
1502
1504
FIGURE 13
FIGURE 14

ULTRASOUND IMAGING PROBE WITH A TRANSDUCER ARRAY WITH A SHEAR-WAVE-MITIGATED COMPOUND LENS

FIELD

The following generally relates to ultrasound imaging and more particularly to an ultrasound imaging probe with a transducer array with a shear-wave-mitigated compound lens.

BACKGROUND

Ultrasound imaging provides a real-time image with information about the interior of an object or a subject such as tissue, organs, etc. With one example, a transmit beamformer provides an excitation pulse to at least a sub-set of the elements of the transducer array. The at least the sub-set of the elements of the transducer array converts the electrical pulse to an ultrasound pressure wave. The ultrasound pressure wave is emitted by the transducer array during a transmit operation, propagates in a medium in a field of view, and interacts with the medium therein. Such interaction results in, among other things, echoes, which are reflections back towards the transducer array.

The transducer array receives the echoes during a receive operation and converts the reflections into analog radio frequency (RF) signals. For each receive operation, the analog RF signals are amplified, converted to digital signals, and beamformed to produce a scan line of RF data. With delay-and-sum beamforming, the digital signals are time delayed, weighted, and then summed to produce the scan lines. The scan lines are further processed (e.g., band-pass filtering, envelope detection, logarithmic compression, etc.), scan converted, and displayed as frame/2-D image (e.g., a B-mode image).

The transducer array assembly generally includes, in addition to the transducer array, a backing layer configured to provide structural support and absorb reflected waves, an interconnect to route signals, one or more acoustic matching layers configured to improve energy transfer between the transducer array and a patient being scanned (where the combination of the interconnect, the transducer array and matching layer(s) is also referred to as an acoustic stack), and an acoustic lens configured to focus the ultrasound pressure waves.

With one ultrasound imaging probe, the acoustic lens has included a room-temperature-vulcanization (RTV) silicone. However, RTV silicones are vapor permeable. As a consequence, such lenses are not well-suited for ultrasound imaging probes employed for surgical procedure as these probes come into contact with biological materials during such procedures and some reprocessing processes (cleaning, disinfection and sterilization) utilizes chemicals that contact and degrade RTV silicones and, hence, the lens, which could reduce the operational lifespan of the ultrasound imaging probe.

With another ultrasound imaging probe, the acoustic lens has included a thermoplastic material such as polymethylpentene, which is commonly referred to as TPX™, a product of Mitsui Chemicals, Tokyo, Japan. TPX is impervious to biological materials and chemical cleaners, unlike RTV, and, thus, better suited for procedures involving biological materials and cleaning processes involving chemicals. However, to focus through TPX either an outer surface of the lens must be concave in elevation or the acoustic stack must be curved in elevation because a velocity of sound in TPX is higher than in tissue.

FIG. 1 illustrates an example of the former with a backing layer 102, an acoustic stack 104 and a plano-concave TPX lens 106 with a concave outer surface 108. Unfortunately, a concave outer surface compromises contact of the outer surface 108 with the patient. FIG. 2 illustrates an example of the latter with a backing layer 202, a curved acoustic stack 204 and a TPX lens 206 with a flat outer surface 208. Unfortunately, a curved acoustic stack restricts process and material options. For example, the curved acoustic stack 204 is amenable to a piezo-composite; however, the curved acoustic stack 204 precludes a solid piezoelectric (e.g., a single crystal) or Capacitive Micromachined Ultrasonic Transducer (CMUT) active layer.

With another ultrasound imaging probe, the acoustic lens has included a compound lens (two or more layers) with an inner layer and an outer layer. FIG. 3 illustrates an example with a backing layer 402, a flat acoustic stack 404, and a compound lens 406 with a plano-convex inner RTV lens 408 and a concave-plano outer TPX lens 410 with a flat outer surface 412. The configuration of FIG. 3 allows for a flat acoustic stack in elevation, and the external TPX layer provides a chemical barrier and outer surface that enables good patient surface contact. In addition, both RTV and TPX have relatively low attenuation for the desired longitudinal waves. However, oblique waves in the RTV produce unwanted shear acoustic waves in the TPX at the RTV-TPX interface, and TPX also has relatively low attenuation for shear acoustic waves. The magnitude of the shear wave depends on the material properties and the angle of incidence, and more energy couples into shear waves as the angle of incidence increases. In general, unwanted shear acoustic waves can introduce unwanted signal that reflects off of reflectors, producing echoes that are received by the transducer array, and manifest as noise in the beamformed image.

An example of longitudinal and shear wave production and propagation is illustrated in FIG. 4. In FIG. 4, an element 502 of the transducer array of the acoustic stack 404 is excited to emit a spherical pressure wave 506, which propagates through the RTV inner lens 408. The spherical pressure wave 506 is shown at a particular instance in time and will continue to grow and propagate. For explanatory and clarity purpose, FIG. 4 shows only a single longitudinal ray 508 of the spherical pressure wave 506. The longitudinal ray 508 refracts through an interface 510 between the RTV inner lens 408 and the TPX outer lens 410, producing a shear wave, having a shear wave ray 512 and a refracted longitudinal wave ray 514.

The refracted longitudinal wave ray 514 propagates in the outer TPX lens 410 and refracts again at an interface 516 between the TPX outer lens 410 and tissue 518, producing the refracted longitudinal ray 520. The shear wave ray 512 also propagates in the TPX outer lens 410 and refracts at the interface 516 between the TPX outer lens 410 and the tissue 518, producing an unwanted longitudinal ray 522. Both the refracted longitudinal ray 520 and the unwanted longitudinal ray 522 propagate in the tissue 518 and interact with reflectors, and the interaction with the unwanted longitudinal ray 522 will produce unwanted echoes.

FIG. 5 shows the longitudinal and shear waves in terms of energy at a particular instance in time from a Finite Element Analysis (FEA), which predicts a behavior of the longitudinal and shear waves. In FIG. 5, an energy 602 in a region 604 corresponds to desired longitudinal rays (e.g., including the ray 520), and an energy 606 in a region 608 corresponds to unwanted longitudinal rays (e.g., including the ray 522). Again, unwanted echoes of unwanted longitudinal rays will be sensed by the transducer array of the acoustic stack 404 and processed along with the desired echoes by front and back end electronics, and may manifest as noise in the beamformed image, degrading diagnostic image quality.

In view of at least the foregoing, there is an unresolved need for an improved acoustic lens for an ultrasound imaging transducer array.

SUMMARY

Aspects of the application address the above matters, and others. This summary introduces concepts that are described in more detail in the detailed description. It should not be used to identify essential features of the claimed subject matter, nor to limit the scope of the claimed subject matter.

In one aspect, an ultrasound imaging probe includes a backing layer, an acoustic stack and a compound lens. The acoustic stack includes an interconnect coupled to the backing layer, a transducer array electrically coupled interconnect and including at least one transducer element with a transducing surface, and at least one matching layer with a first side acoustically coupled to the transducing surface and a second opposing side. The compound lens includes an inner lens with a planer inner side acoustically coupled to the second opposing side of the matching layer and a first non-flat side that is non-flat in elevation and wavy at least in azimuth. The compound lens further includes an outer lens with an outer side configured to contact a subject or object and a second non-flat side that is non-flat in elevation and wavy at least in azimuth. The first non-flat side of the inner lens is acoustically coupled to the second non-flat side of the outer lens.

In one instance, a first wavy pattern of the first non-flat side of the inner lens in azimuth is sinusoidal, a second wavy pattern of the second wavy side of the second non-flat side of the outer lens in azimuth is sinusoidal, and the first wavy sinusoidal pattern and the second wavy sinusoidal pattern are complementary patterns. In another instance, a first wavy pattern of the first non-flat side of the inner lens in azimuth is triangular, a second wavy pattern of the second wavy side of the second non-flat side of the outer lens in azimuth is triangular, and the first wavy sinusoidal pattern and the second wavy sinusoidal pattern are complementary patterns.

In another instance, a first wavy pattern of the first non-flat side of the inner lens in azimuth is sawtooth, a second wavy pattern of the second wavy side of the second non-flat side of the outer lens in azimuth is sawtooth, and the first wavy sinusoidal pattern and the second wavy sinusoidal pattern are complementary patterns. In another instance, a first wavy pattern of the first non-flat side of the inner lens in azimuth is a square wave, a second wavy pattern of the second wavy side of the second non-flat side of the outer lens in azimuth is a square wave, and the first wavy sinusoidal pattern and the second wavy sinusoidal pattern are complementary patterns.

In another instance, at least one of a first height of first waves in a first wavy pattern of the first non-flat side of the inner lens in azimuth and a second height of second waves in a second wavy pattern of the second non-flat side of the outer lens is a half wavelength. In another instance, at least one of a first pitch of first waves in a first wavy pattern of the first non-flat side of the inner lens in azimuth and a second pitch of second waves in a second wavy pattern of the second non-flat side of the outer lens is a half wavelength.

In another instance, the outer lens includes a polymethylpentene. In another instance, the inner lens includes at least one of a polyurethane and a room-temperature-vulcanization (RTV) silicone. In another instance, the compound lens has a fixed depth focus in elevation. In another instance, a wavy interface between the first non-flat side of the inner lens in azimuth and the second non-flat side of the outer lens in azimuth is configured to trap shear waves. In another instance, a wavy interface between the first non-flat side of the inner lens in azimuth and the second non-flat side of the outer lens in azimuth is configured to produce destructive shear waves.

In another aspect, an ultrasound imaging system includes an ultrasound imaging probe and a console. The ultrasound imaging probe includes a backing layer, an acoustic stack and a compound lens. The acoustic stack includes an interconnect coupled to the backing layer, a transducer array electrically coupled interconnect and including at least one transducer element with a transducing surface, and at least one matching layer with a first side acoustically coupled to the transducing surface and a second opposing side. The compound lens includes an inner lens with a planer inner side acoustically coupled to the second opposing side of the matching layer and a first non-flat side that is non-flat in elevation and wavy at least in azimuth. The compound lens further includes an outer lens with an outer side configured to contact a subject or object and a second non-flat side that is non-flat in elevation and wavy at least in azimuth. The first non-flat side of the inner lens is acoustically coupled to the second non-flat side of the outer lens. The console includes transmit circuitry that conveys an excitation pulse to the transducer array, receive circuitry that receives a signal indicative of an ultrasound echo from the transducer array, and a beamformer that processes the received signal, generating ultrasound image data.

In one instance, the outer lens includes a polymethylpentene and the inner lens includes at least one of a polyurethane and a room-temperature-vulcanization (RTV) silicone. In another instance, a wavy interface between the inner lens and the outer lens in azimuth is configured to at least one of trap shear waves and produce destructive shear waves. In another instance, a height of waves in a pattern of the first and second lenses is a half wavelength, and a pitch of the waves in the pattern of the first and second lenses is a half wavelength.

In another aspect, a method includes transmitting an ultrasound pressure wave in a compound lens of an ultrasound imaging probe. The compound lens includes an inner lens with a first wavy surface in azimuth and an outer lens with a second wavy surface in azimuth, and the first wavy surface is coupled to the second wavy surface. The method further includes receiving an echo signal with the ultrasound imaging probe. The method further includes beamforming the echo signal to create an image. The method further includes displaying the image.

In one instance, the method further includes creating a shear pressure wave resonator at an interface between the first wavy surface coupled to the second wavy surface. In another instance, the method further includes producing destructive shear pressure waves at an interface between the first wavy surface coupled to the second wavy surface. In another instance, the method further includes producing destructive shear pressure waves at an interface between the first wavy surface coupled to the second wavy surface.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

FIG. 11 graphically illustrates an energy map of desired longitudinal waves in a prior art compound lens with a smooth interface between the inner and the outer lenses.

FIG. 12 graphically illustrates an energy map of unwanted shear waves in a prior art compound lens with a smooth interface between the inner and the outer lenses.

FIG. 13 graphically illustrates an energy map of desired longitudinal waves in the compound lens with the wavy interface described herein, in accordance with an aspect of an embodiment(s) herein.

FIG. 14 graphically illustrates an energy map of unwanted shear waves in the compound lens with the wavy interface described herein, in accordance with an aspect of an embodiment(s) herein.

DETAILED DESCRIPTION

Embodiments of the present disclosure will now be described, by way of example, with reference to the figures, in which an ultrasound imaging probe includes a transducer array assembly with a compound lens with at least an inner lens and an outer lens configured to mitigate shear waves. The inner lens includes a planar back coupled to an acoustic stack. The planar back allows for a planar acoustic stack. As such, the acoustic stack can include a piezo-composite, a solid piezoelectric (e.g., a single crystal), a CMUT, and/or other active layer, and is not limited to processes and/or materials for curved acoustic stack.

The outer lens includes a front, which could be planar, convex, etc. This allows for substantial contact of an area of the outer lens and a patient being scanned. The outer lens also includes TPX, which, again, is impervious to the biological materials and chemical cleaners, rendering the ultrasound imaging probe is well-suited for procedures involving biological materials and cleaning processes involving chemicals. The inner layer includes a material with relatively low attenuation of the longitudinal wave and that reduces an impedance mismatch with TPX, such as an RTV silicone, a polyurethane, etc.

As discussed above, the interface between such an inner lens (e.g., with an RTV silicone, etc.) and the TPX outer lens produces unwanted shear acoustic waves, TPX has relatively low attenuation for shear acoustic waves, and the unwanted shear acoustic waves can lead to unwanted longitudinal waves and degradation of image quality, e.g., where the unwanted acoustic waves reach reflectors in the field of view and echoes created via the interaction are received by the transducer array and utilized, along with desired echoes from the desired longitudinal waves, to generate an image.

As described in greater detail below, the compound lens herein includes a wavy interface between the inner lens and the outer lens, which creates shear wave resonators at the interface and/or causes destructive interference of shear waves, both of which reduce a magnitude of an energy of the shear waves, overcoming a deficiency of existing ultrasound imaging probes, e.g., at least the deficiency discussed above.

Figure 6:
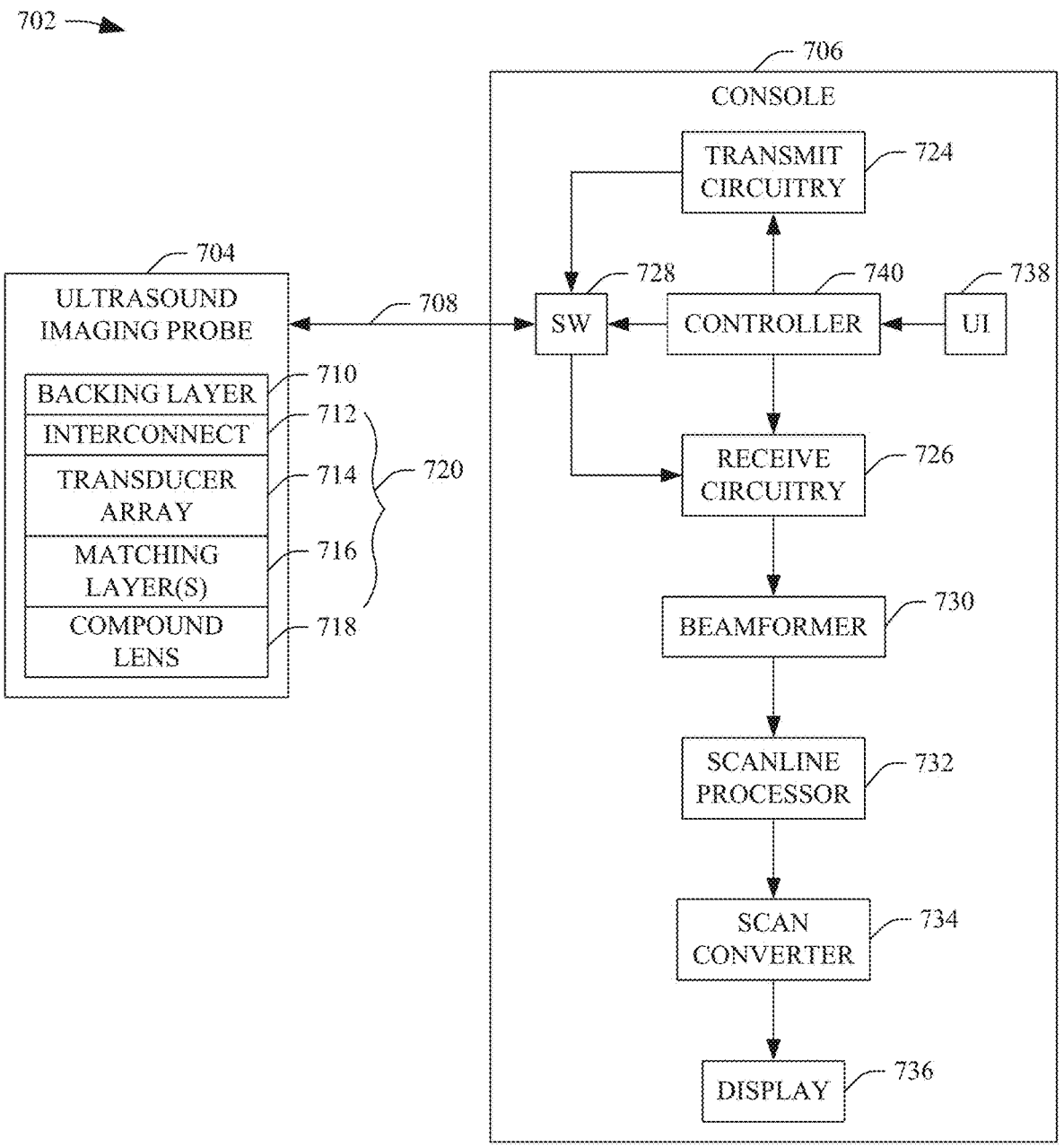
FIG. 6 schematically illustrates an example system configured for ultrasound imaging, in accordance with an aspect of an embodiment(s) herein.

Turning to FIG. 6, a non-limiting example of an ultrasound imaging system 702 is schematically illustrated. The ultrasound imaging system 702 includes an ultrasound imaging probe 704 and a console 706. In the illustrated embodiment, the ultrasound imaging probe 704 and the console 706 interface with each other via a communication channel 708. In one instance the communication channel 708 includes wired technology, e.g., complimentary interfaces and a cable therebetween. In another instance the communication channel 708 includes wireless technology, e.g., Wi-Fi, etc. In yet another instance the communication channel 708 includes a combination of wired and wireless technology. In yet another instance, the ultrasound imaging probe 704 and the console 706 are integrated in a same housing such as part of a hand-held ultrasound system, etc.

The ultrasound imaging probe 704 includes at least a backing layer 710, an interconnect 712, a transducer array 714, at least one matching layer 716, and a compound lens 718, where a combination of the interconnect 712, the transducer array 714 and the at least one matching layer 716 are also referred to herein as an acoustic stack 720. In general, the backing layer 710 provides mechanical support for the transducer array 714, the interconnect 712 routes electrical signals produced by the transducer array 714 for processing, the at least one matching layer 716 acoustically couples acoustic energy from the transducer array 714 to transmission medium, and the compound lens 718 focuses the acoustic energy. Optionally, the ultrasound imaging probe 704 may include an acoustic window configured to provide a structural interface between the probe 704 and an object or subject to be or being scanned.

The transducer array 714 includes a one or two-dimensional array of at least one transducer element. Examples of suitable arrays include sector, linear, curved, square, rectangular, circular, irregular, and/or other shaped arrays. Examples of suitable elements include piezo-composite, solid piezoelectric (e.g., a single crystal), CMUT, and/or other ultrasound imaging transducer elements. Examples of a suitable number of the at least element includes 64, 128, 192, 256, larger, in between and/or smaller arrays. The at least element is configured to transmit a pressure wave, receive echo signals that are generated in response to the pressure wave interacting with reflectors, and generate electrical signals indicative thereof.

The compound lens 718 includes at least an inner lens coupled to an outer lens to mitigate shear waves produced and propagating in the compound lens 718. As described in greater detail below, this includes configuring the inner and outer lenses such that an interface therebetween has a non-planar shape, e.g., a wavy shape. In this instance, the interface between the inner lens and the outer lens creates shear wave resonators at the interface and/or causes destructive interference of shear waves, both of which reduce a magnitude of an energy of the shear waves, overcoming a deficiency of existing ultrasound imaging probes, e.g., at least the deficiency discussed above.

The inner lens includes a planar back coupled to an acoustic stack. The planar back allows for a planar acoustic stack. As such, the acoustic stack can include a piezo-composite, a solid piezoelectric (e.g., a single crystal), a CMUT, and/or other active layer, and is not limited to processes and/or materials for curved acoustic stack. The inner lens may include RTV, a polyurethane, etc. The outer lens includes a front, which could be planar, convex, etc. This allows for substantial contact of an area of the outer lens and a patient being scanned. The outer lens further includes TPX, which, again, is impervious to the biological materials and chemical cleaners, and, thus, is well-suited for procedures involving biological materials and cleaning processes involving chemicals.

The console 706 includes a transmit circuitry 724 configured to generate the excitation electrical signal provided to transducer array 714 for transmitting the ultrasound pressure field. In one instance, this includes generating delays to individual elements of the at least one element of the transducer array 714, e.g., for transmit focusing, beam steering, etc.

The console 706 further includes a receive circuitry 726 configured to receive the analog electrical signals from the at least one element and pre-process the analog electrical signals, e.g., amplify, digitize, focus, and/or otherwise process the analog electrical signals. For example, in one instance the receive circuit 726 includes an amplifier and a corresponding analog to digital converter (ADC) for each element, where each amplifier amplifies a corresponding analog electrical signal from a micro-volt level to a voltage range of the ADC.

The console 706 further includes a switch ("SW") 728 configured to switch between the transmit circuitry 724 and the receive circuitry 726, e.g., by electrically connecting the transmit circuitry 724 to the transducer array 714 for a transmit operation and electrically connecting the receive circuitry 726 to the transducer array 714 for a receive operation. In an alternative instance, separate switches are employed for each of the transmit circuitry 724 and the receive circuitry 726.

The console 706 further includes a beamformer 730. For receive operations, the beamformer 730 is configured to beamform, e.g., via delay-and-sum (e.g., a matched-filter beamformer, etc.) and/or other beamforming, the signals from the receive circuitry 726 and construct radiofrequency (RF) data for the echoes for each receive operation. With delay-and-sum beamforming, the digital signal for each element is delayed to align the signals in time, amplified, and then summed. In one instance, a matched filter matched to an expected received echo-pulse shape (bandwidth) operates on the signals.

The console 706 further includes a scanline processor 732. When configured for I/Q demodulation, the scanline processor 732 down mixes the RF signal and optionally applies low pass filtering and/or decimation. This may include employing a Hilbert Transform, a combination of a Complex-Demodulation Band Pass Filter and optional decimation, and/or other processing. The scanline processor 732 detects, extracts and outputs an envelope (i.e., an amplitude) of the I/Q signal (or the RF signal where I/Q modulation is omitted). In one instance, this is achieved using a Hilbert Transform and/or other approach.

The scanline processor 732 compresses the extracted envelope, reducing the dynamic range, e.g., to reduce the dynamic range to a predetermined display precision by a logarithmic (log)-based dynamic range compression and/or otherwise, and outputs a scanline. The scanline processor 732 outputs the processed scanlines as a frame/image (e.g., a B-mode image). The scanline processor 732 may apply other processing such as filtering (e.g., via a Finite Impulse Response (FIR) filter, an Infinite Impulse Response (IIR) filter, etc.), time gain compensation (TGC), noise rejection, and/or other processing.

The console 706 further includes a scan converter 734 and a display 736. The scan converter 734 is configured to scan convert the compounded image into a coordinate system of the display 736. The scan converter 734 can be configured to employ analog and/or digital scan converting techniques. The scan converted data can be displayed on the display 736 and/or other display monitor.

The console 706 further includes a user interface ("UI") 738. The user interface 738 includes one or more input devices (such as a button, a knob, a slider, a touch screen, a mouse, a keyboard, etc.) and/or other input device, and/or one or more output devices such as a visible, audible, etc. indicator. The user interface 738 allows a user to control an operation of the system 702. For example, in one instance, the user interface 738 receives an input indicative of an imaging protocol, etc.

The console 706 further includes a controller 740. The controller 740 includes a processor(s) such as a microprocessor (μP), a central processing unit (CPU), a graphics processing unit (GPU), etc., and memory, which stores the adaptive spatial compounding algorithm described herein. The controller 740 is configured to control one or more of the transmit circuitry 724, the receive circuitry 726, the switch 728, the beamformer 730, the scanline processor 732, the scan converter 734, the display 736, and/or the user interface 738. One or more of these components of the console 706 can be implemented in software and/or hardware.

Although the console 706 is described above as separate from and interfaced with the ultrasound imaging probe 704, it is to be understood that some or all of the components and/or functions provided by the console 706 can be contained within the ultrasound imaging probe 704 instead of in the separate console 706. For example, in one instance the transducer array 704 includes a 2-D array with transmit circuitry, a switch, receive circuitry, and a first stage of beamforming, all within the ultrasound imaging probe 704. In another instance, where the ultrasound imaging probe 704 is configured as a 1-D handheld probe, one or more of the components and/or functions are within a handle of the ultrasound imaging probe 704. Other configurations in which at least some of these functions are part of the ultrasound imaging probe 704 and/or outside of the console 706 are contemplated herein.

Figure 7:
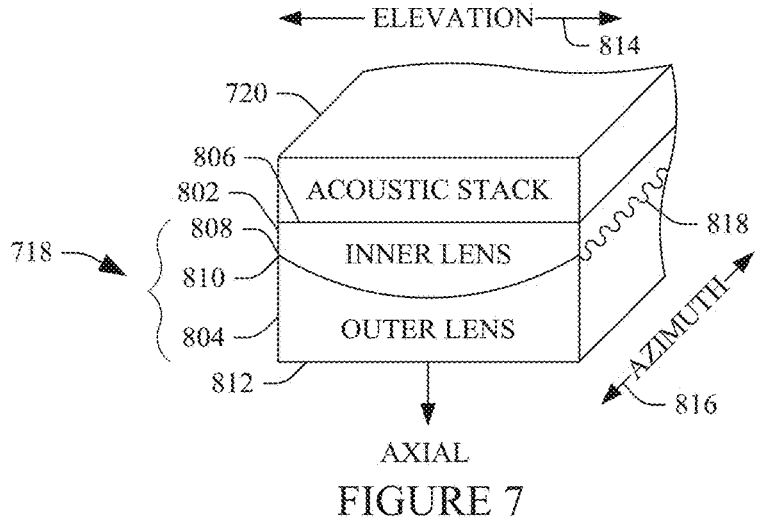
FIG. 7 schematically illustrates a perspective view of a compound lens with a wavy interface between lenses in azimuth in connection with an acoustic stack, in accordance with an aspect of an embodiment(s) herein.
Figure 8:
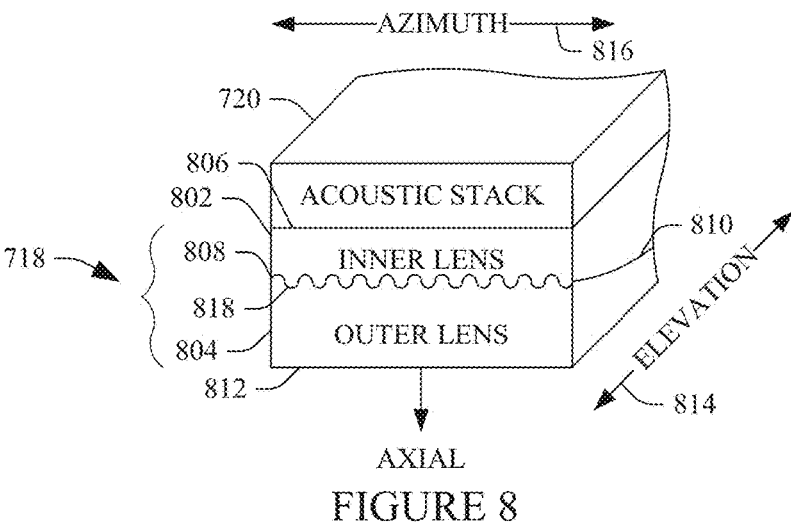
FIG. 8 schematically illustrates another perspective view of the compound lens with the wavy interface between lenses in azimuth in connection with the acoustic stack, in accordance with an aspect of an embodiment(s) herein.

As briefly described above, the compound lens 718 includes at least an inner lens coupled to an outer lens to mitigate shear waves produced and propagating in the compound lens 718. FIGS. 7 and 8 schematically illustrate perspective views of an example configuration of the compound lens 718 in connection with the acoustic stack 720. FIG. 7 schematically illustrates a perspective view in elevation, and FIG. 8 schematically illustrates a perspective view in azimuth. In this example, the compound lens 718 includes an inner lens 802 and an outer lens 804. In another example, the compound lens 718 includes more than two lenses. The inner lens 802 includes a flat side 806 and a non-flat side 808, which diametrically opposes the flat side 806. The outer lens 804 includes a non-flat side 810 and an opposing flat side 812, which diametrically opposes the non-flat side 810.

Figure 1:
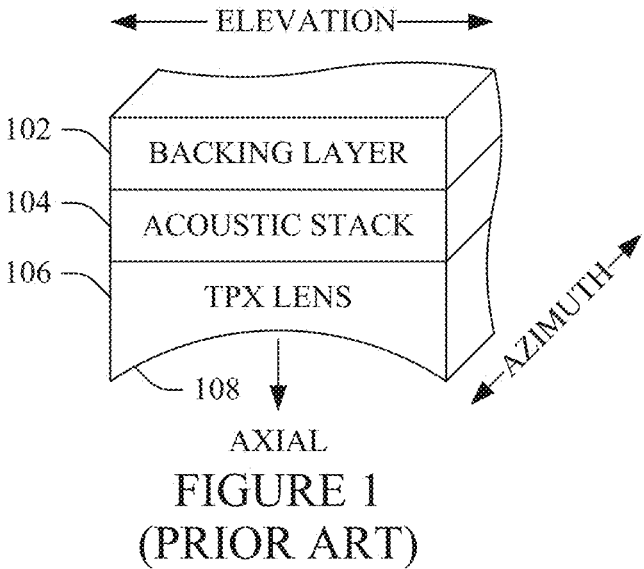
FIG. 1 shows a prior art example ultrasound imaging probe including a flat acoustic stack and a plano-concave TPX lens.
Figure 2:
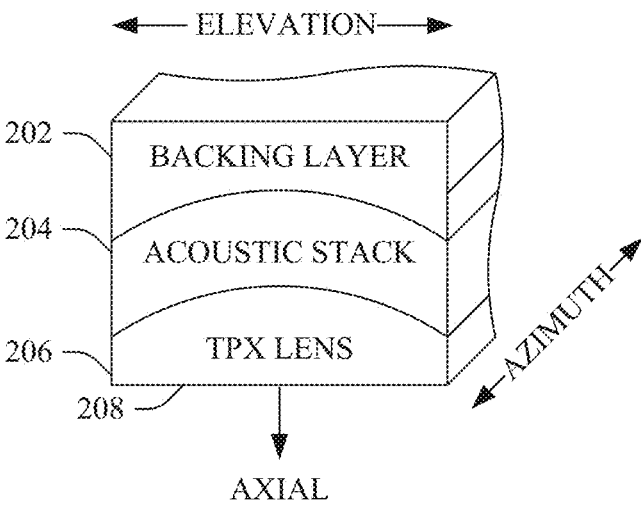
FIG. 2 shows a prior art example ultrasound imaging probe including a curved acoustic stack and a concave-plano TPX lens.
Figure 3:
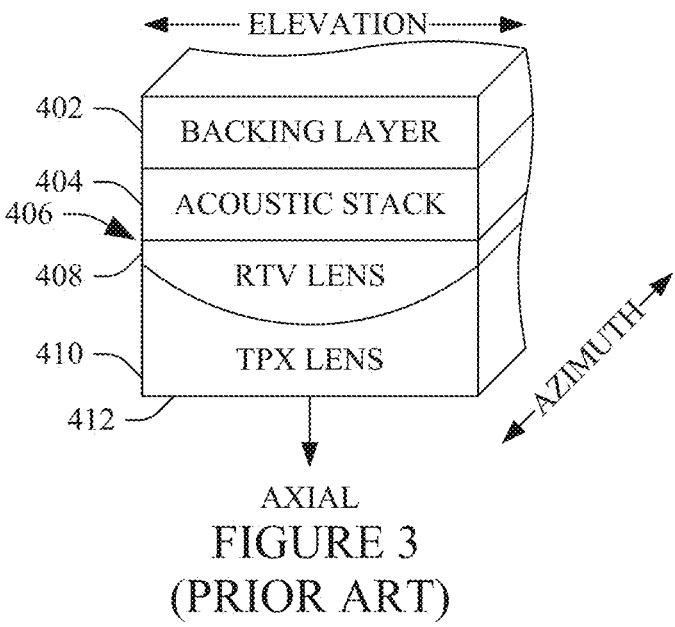
FIG. 3 shows another prior art example of an ultrasound imaging probe including a flat acoustic stack and a compound lens (RTV-TPX) susceptible to producing unwanted shear pressure waves.
Figure 4:
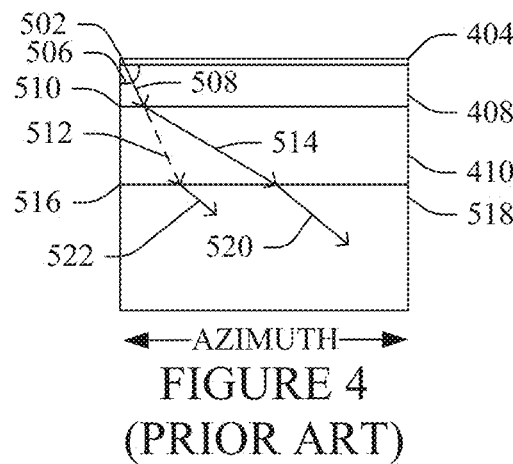
FIG. 4 shows an example of unwanted shear pressure wave production at an interface between two lenses of a compound lens of a transducer array.

The flat side 806 of the inner lens 802 is acoustically coupled to the acoustic stack 720. In one instance, the flatness of the flat side 806 allows for a flat acoustic stack 720. As such, the acoustic stack 720 can include a piezo-composite, a solid piezoelectric (e.g., a single crystal), a CMUT, and/or other active layer, and is not limited to processes and/or materials for curved acoustic stack. The flat side 812 of the outer lens 804 provides a flat outer surface. In one instance, the flatness of the flat side 812 allows for substantial contact between the ultrasound signal transmitting and receiving region and the patient being scanned, e.g., relative to the curved outer surface 108 illustrated in FIG. 1.

The non-flat side 808 of the inner lens 802 is convex in elevation 814, and the non-flat side 810 of the outer lens 804 is concave in elevation 814. The non-flat side 808 of the inner lens 802 is acoustically coupled to the non-flat side 810 of the outer lens 804. The radius of curvature of the non-flat (convex) side 808 of the inner lens 802 and the non-flat (concave) side 810 of the outer lens 804 provides a predetermined fixed passive focus in elevation.

The non-flat side 808 of the inner lens 802 is wavy in azimuth 816, and the non-flat side 810 of the outer lens 804 is also wavy in azimuth 816. Again, the non-flat side 808 of the inner lens 802 is acoustically coupled to the non-flat side 810 of the outer lens 804. A pattern of a waviness of a surface of the non-flat side 808 of the inner lens 802 in azimuth 816 is complementary to a pattern of a waviness of a surface of the non-flat side 810 of the outer lens 804 in azimuth 816 and provides a wavy interface 818 between the inner and outer lenses 802 and 804. In this example, a pattern of the waviness includes a sinusoidal pattern. Other patterns are contemplated herein, including examples discussed in connection with FIGS. 18, 19 and 20 below.

The wavy interface 818 mitigates unwanted shear waves produced at the interface 818 between the inner and outer lenses 802 and 804. Briefly turning to FIG. 9, a magnified view of a portion of the wavy interface 818 in connection with rays 902 of a pressure wave impinging on the wavy interface 818 is schematically illustrated. In one instance, a pattern of waviness of the wavy interface 818 creates resonators for the shear waves that trap shear wave energy at the wavy interface 818. Additionally, or alternatively, the varying incidence angles of the rays of the pressure wave result in a varying magnitude and/or phase of the shear waves, causing destructive interference that cancels shear waves. Individually, or in combination, the overall affect is a reduced magnitude of unwanted signal from shear waves.

In FIGS. 7 and 8, the non-flat side 808 of the inner lens 802 is convex in elevation 814, and the non-flat side 810 of the outer lens 804 is concave in elevation 814. In another embodiment, the non-flat side 808 of the inner lens 802 is wavy in elevation 814, and the non-flat side 810 of the outer lens 804 is wavy in elevation 814, e.g., similar to the non-flat side 808 of the inner lens 802 in azimuth 816, and the non-flat side 810 of the outer lens 804 is in azimuth 816. In one instance, the wavy pattern in azimuth 816 and in elevation 814 is a same or similar wavy pattern. In another instance, the wavy pattern in azimuth 816 and in elevation 814 are different wavy patterns. In general, the non-flat sides 808 and/or 810 in elevation 814 and/or in in azimuth 816, in one instance, can be any shape other than flat.

Figure 9:
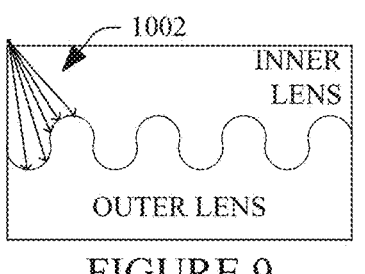
FIG. 9 illustrates a magnified view of a portion of the wavy interface in FIGS. 7 and 8, in accordance with an aspect of an embodiment(s) herein.
Figure 10:
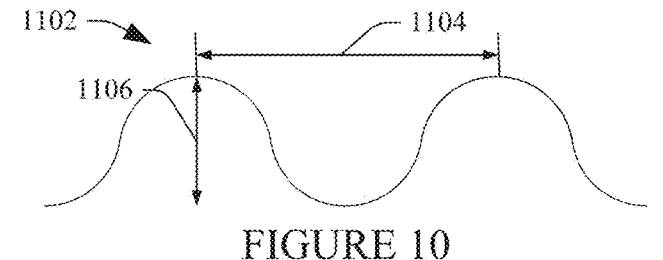
FIG. 10 illustrates a magnified view of a single wave of the wavy interface in FIGS. 8 and 9, in accordance with an aspect of an embodiment(s) herein.

Briefly turning to FIG. 10, a magnified view of a pattern of waviness 1102 of the wavy interface 818 in FIGS. 7, 8 and 9 is schematically illustrated. In one instance, a pitch 1104 between waves of the pattern of the wavy interface 818 is half a wavelength $$\left(\frac{1}{2}\lambda\right),$$

and a height 1106 of a wave of the pattern of the wavy interface 818 is half a wavelength $$\left(\frac{1}{2}\lambda\right).$$

Figure 18:
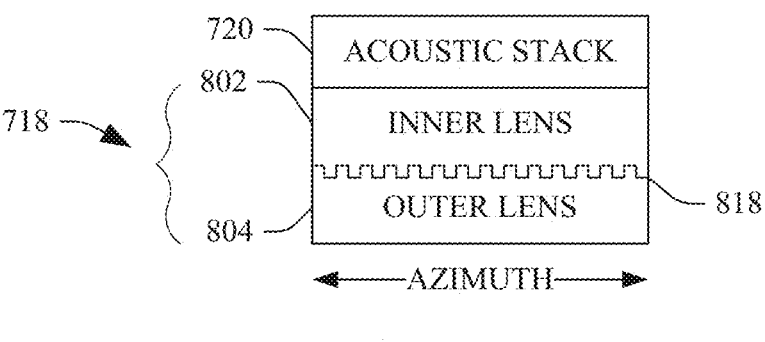
FIG. 18 schematically illustrates another wavy interface between the lenses of the compound lens described herein, in accordance with an aspect of an embodiment(s) herein.
Figure 19:
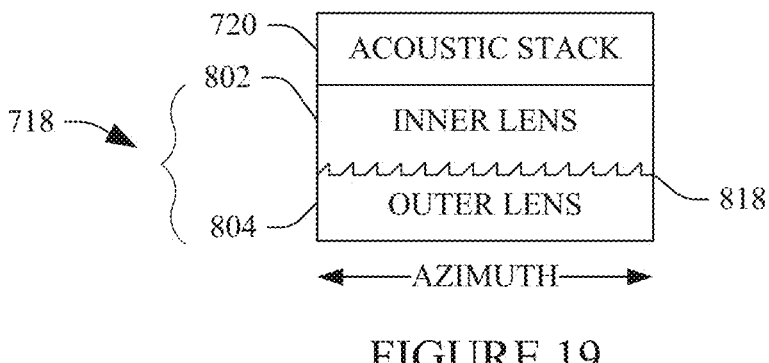
FIG. 19 schematically illustrates yet another wavy interface between the lenses of the compound lens described herein, in accordance with an aspect of an embodiment(s) herein.
Figure 20:
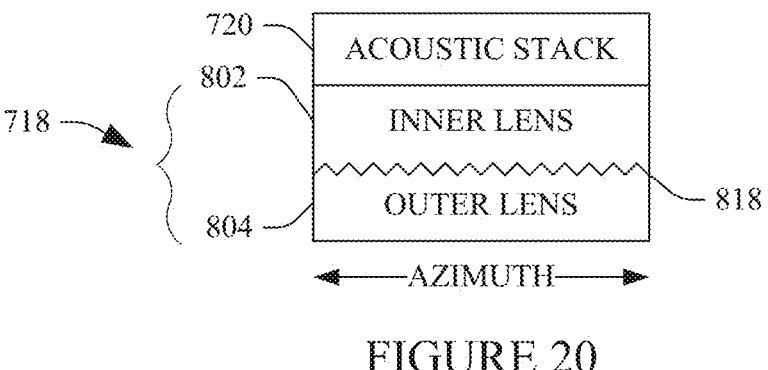
FIG. 20 schematically illustrates still another wavy interface between the lenses of the compound lens described herein, in accordance with an aspect of an embodiment(s) herein.

In other instances, the pitch 1104 and/or the height 1106 is different, including greater or less. In one instance, the pattern of the wavy interface 818 is repeated throughout the pattern. In another instance, one or more of the waves can be different, including a different pitch, a different height, a different shape, etc. FIGS. 18-20, which will be discussed below, illustrate non-limiting examples of other suitable patterns.

FIGS. 11, 12, 13 and 14 graphically illustrate energy mappings without (FIGS. 11 and 12) and with (FIGS. 13 and 14) the compound lens 718 (FIG. 6). FIG. 11 graphically illustrates an energy map of desired longitudinal waves in a compound lens with a smooth interface between the inner and the outer lenses, and FIG. 13 graphically illustrates an energy map of unwanted shear waves in a compound lens with the smooth interface between the inner and the outer lenses. FIG. 13 graphically illustrates an energy map of desired longitudinal waves in the compound lens 718 described herein, and FIG. 14 graphically illustrates an energy map of unwanted shear waves in the compound lens 718 described herein.

Initially referring to FIGS. 11 and 12, an energy map 1202 corresponds to a longitudinal pressure wave propagating through an inner lens 1204. At an interface 1206 between the inner lens 1204 and an outer lens 1208, the longitudinal pressure wave refracts and shear waves are produced. In FIG. 11, an energy map 1210 corresponds to the refracted longitudinal pressure wave propagating through the outer lens 1208. In FIG. 12, an energy map 1302 corresponds to the shear wave propagating through the outer lens 1208.

Turning to FIGS. 13 and 14, an energy map 1402 corresponds to a longitudinal pressure wave propagating through the inner lens 802. At the wavy interface 818 between the inner lens 802 and an outer lens 804, the longitudinal pressure wave refracts and shear waves are produced. In FIG. 13, an energy map 1404 corresponds to the refracted longitudinal pressure wave propagating through the outer lens 804. In FIG. 14, an energy map 1502 corresponds to the shear wave propagating through the outer lens 804.

From FIGS. 11 and 13, the compound lens 718 minimally affects longitudinal pressure wave, as seen by comparing the energy maps 1210 and 1404. In other words, the compound lens 718 minimally affects the longitudinal pressure wave, relative to using a compound lens with a smooth surface between lenses rather than the compound lens 718 described herein. From FIGS. 12 and 14, the compound lens 718 more significantly affects the shear wave, as seen by comparing the energy maps 1302 and 1502. That is, the compound lens 718 can reduce a magnitude of an energy of the shear waves. FIG. 14 further shows shear wave resonance 1504 created at the wavy interface 818, which reduces an energy of the shear waves, as discussed herein.

Figure 5:
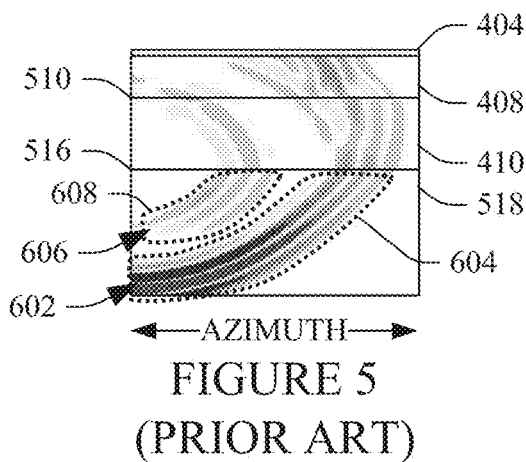
FIG. 5 shows example energy maps corresponding to unwanted shear pressure waves and desired longitudinal pressure waves.
Figure 15:
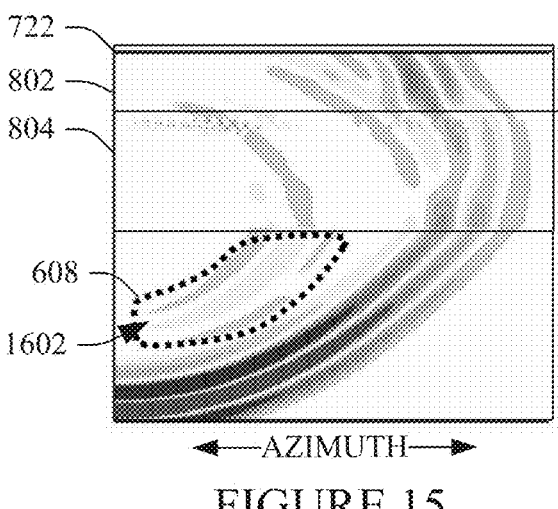
FIG. 15 shows an example of the region of FIG. 5 corresponding to unwanted shear pressure wave energy with reduced unwanted shear pressure wave energy due to the compound lens described herein, in accordance with an aspect of an embodiment(s) herein.
Figure 16:
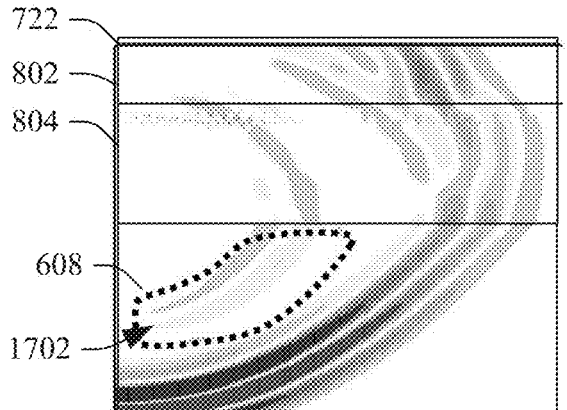
FIG. 16 shows another example of the region of FIG. 5 corresponding to unwanted shear pressure wave energy with reduced unwanted shear pressure wave energy due to the compound lens described herein, in accordance with an aspect of an embodiment(s) herein.
Figure 17:
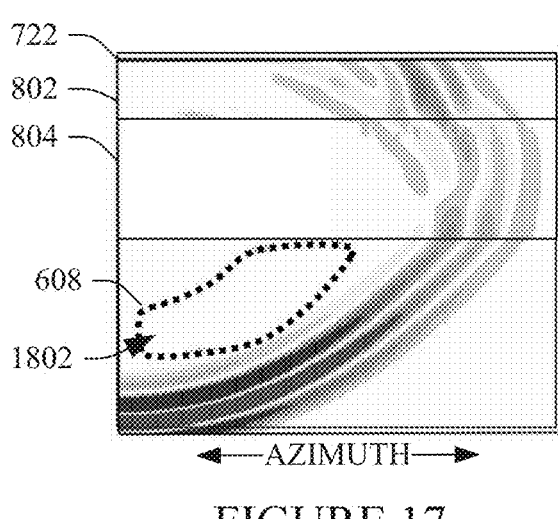
FIG. 17 shows yet another example of the region of FIG. 5 corresponding to unwanted shear pressure wave energy with reduced unwanted shear pressure wave energy due to the compound lens described herein, in accordance with an aspect of an embodiment(s) herein.

FIG. 15 shows an example of the region 608 of FIG. 5 corresponding to unwanted shear wave energy 606 with a reduced unwanted shear wave energy 1602 due to the compound lens 718. FIG. 16 shows another example of the region 608 of FIG. 5 corresponding to unwanted shear pressure wave energy 606 with further reduced unwanted shear pressure wave energy 1702 due to the compound lens 718. FIG. 17 shows another example of the region 608 of FIG. 5 corresponding to unwanted shear wave energy 606 with further reduced unwanted shear wave energy 1802 due to the compound lens 718.

Returning to FIGS. 7 and 8, in one instance, the outer lens 812 includes TPX. Again, TPX is impervious to the biological materials and chemical cleaners and is well-suited for procedures involving biological materials and cleaning processes involving chemicals. The inner lens 802 includes RTV, a polyurethane based lens, etc. In general, the inner lens 802 includes a material with relatively low attenuation of the longitudinal wave, that reduces an impedance mismatch with TPX, etc. As described herein, the flat sides of the inner lens 802 and the outer lens 804 respectively allow for flat acoustic stacks and substantial surface area contact between the outer lens 804 and the patient. In addition, the wavy interface 818 mitigate shear waves, e.g., through shear wave resonators and/or destructive interference.

In FIGS. 7-9, the wavy interface 818 includes a sinusoidal pattern. FIGS. 18, 19 and 20 schematically illustrate other non-limiting patterns. As discussed herein, a suitable pattern includes a continuously repeating pattern and/or a non-repeating pattern.

FIG. 18 shows an example of another suitable pattern of the wavy interface 818. In this example, the compound lens 718 is coupled to the acoustic stack 720 as described herein and/or otherwise. In this example, a pattern of the wavy interface 818 includes a square wave. FIG. 19 shows an example of yet another suitable pattern of the wavy interface 818. In this example, the compound lens 718 is coupled to the acoustic stack 720 as described herein and/or otherwise. In this example, a pattern of the wavy interface 818 includes a sawtooth wave. FIG. 20 shows an example of still another suitable pattern of the wavy interface 818. In this example, the compound lens 718 is coupled to the acoustic stack 720 as described herein and/or otherwise. In this example, a pattern of the wavy interface 818 includes a triangle wave.

Figure 21:
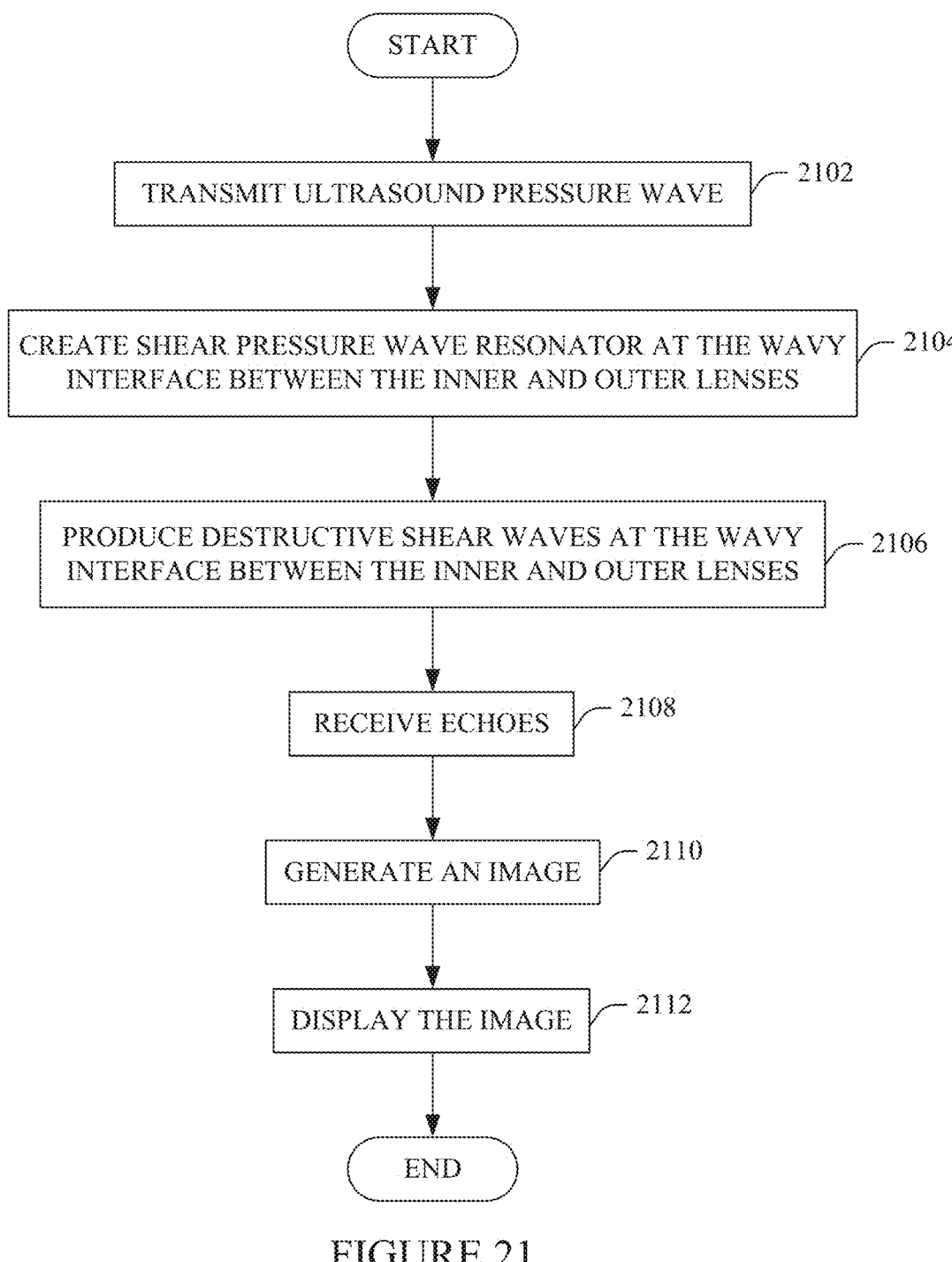
FIG. 21 illustrates another non-limiting example of a flow chart for a computer-implemented method based at least on image characteristics, in accordance with an embodiment(s) herein.

FIG. 21 illustrates a non-limiting example of a flow chart for a computer-implemented method based at least on image characteristics. It is to be appreciated that the ordering of the acts in the method is not limiting. As such, other orderings are contemplated herein. In addition, one or more acts may be omitted, and/or one or more additional acts may be included. At 2102, an ultrasound pressure wave is transmitted in a compound lens of an ultrasound imaging probe, as described herein and/or otherwise. The compound lens includes an inner lens with a first wavy surface in azimuth and an outer lens with a second wavy surface in azimuth, and the first wavy surface is coupled to the second wavy surface.

At 2104, a shear pressure wave resonator is created at a wavy interface between the inner lens and the outer lens, as described herein and/or otherwise. At 2106, the wavy interface produces destructive shear pressure waves, as described herein and/or otherwise. At 2108, an echo signal is received with the ultrasound imaging probe, as described herein and/or otherwise. Echo signals are generated in response to the pressure wave interacting with reflectors. At 2110, the echo signal is beamformed to create an image, as described herein and/or otherwise. At 2112, an image is displayed, as described herein and/or otherwise.

The above can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

Again, embodiments of the present disclosure describe an ultrasound imaging probe that includes a transducer array assembly with a compound lens with at least an inner lens and an outer lens configured to mitigate shear waves. The inner lens includes a planar back coupled to an acoustic stack. The planar back allows for a planar acoustic stack. As such, the acoustic stack can include a piezo-composite, a solid piezoelectric (e.g., a single crystal), a CMUT, and/or other active layer, and is not limited to processes and/or materials for curved acoustic stack.

The outer lens includes a front, which could be planar, convex, etc. . . . This allows for substantial contact of an area of the outer lens and a patient being scanned. The outer lens also includes TPX, which, again, is impervious to the biological materials and chemical cleaners, rendering the ultrasound imaging probe is well-suited for procedures involving biological materials and cleaning processes involving chemicals. The inner layer includes a material with relatively low attenuation of the longitudinal wave and that reduces an impedance mismatch with TPX, such as an RTV silicone, a polyurethane, etc.

As discussed above, the interface between such an inner lens (e.g., with an RTV silicone, etc.) and the TPX outer lens produces unwanted shear acoustic waves, TPX has relatively low attenuation for shear acoustic waves, and the unwanted shear acoustic waves can lead to unwanted longitudinal waves and degradation of image quality, e.g., where the unwanted acoustic waves reach reflectors in the field of view and echoes created via the interaction are received by the transducer array and utilized, along with desired echoes from the desired longitudinal waves, to generate an image.

As described in greater detail herein, the compound lens herein includes a wavy interface between the inner lens and the outer lens, which creates shear wave resonators at the interface and/or causes destructive interference of shear waves, both of which reduce a magnitude of an energy of the shear waves, overcoming a deficiency of existing ultrasound imaging probes, e.g., at least the deficiency discussed above.

For example, in one aspect, an ultrasound imaging probe includes a backing layer, an acoustic stack and a compound lens. The acoustic stack includes an interconnect coupled to the backing layer, a transducer array electrically coupled interconnect and including at least one transducer element with a transducing surface, and at least one matching layer with a first side acoustically coupled to the transducing surface and a second opposing side. The compound lens includes an inner lens with a planer inner side acoustically coupled to the second opposing side of the matching layer and a first non-flat side that is non-flat in elevation and wavy at least in azimuth. The compound lens further includes an outer lens with an outer side configured to contact a subject or object and a second non-flat side that is non-flat in elevation and wavy at least in azimuth. The first non-flat side of the inner lens is acoustically coupled to the second non-flat side of the outer lens.

In another aspect, an ultrasound imaging system includes an ultrasound imaging probe and a console. The ultrasound imaging probe includes a backing layer, an acoustic stack and a compound lens. The acoustic stack includes an interconnect coupled to the backing layer, a transducer array electrically coupled interconnect and including at least one transducer element with a transducing surface, and at least one matching layer with a first side acoustically coupled to the transducing surface and a second opposing side. The compound lens includes an inner lens with a planer inner side acoustically coupled to the second opposing side of the matching layer and a first non-flat side that is non-flat in elevation and wavy at least in azimuth. The compound lens further includes an outer lens with an outer side configured to contact a subject or object and a second non-flat side that is non-flat in elevation and wavy at least in azimuth. The first non-flat side of the inner lens is acoustically coupled to the second non-flat side of the outer lens. The console includes transmit circuitry that conveys an excitation pulse to the transducer array, receive circuitry that receives a signal indicative of an ultrasound echo from the transducer array, and a beamformer that processes the received signal, generating ultrasound image data.

In another aspect, a method includes transmitting an ultrasound pressure wave in a compound lens of an ultrasound imaging probe. The compound lens includes an inner lens with a first wavy surface in azimuth and an outer lens with a second wavy surface in azimuth, and the first wavy surface is coupled to the second wavy surface. The method further includes receiving an echo signal with the ultrasound imaging probe. The method further includes beamforming the echo signal to create an image. The method further includes displaying the image.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include such additional elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only and are thus not intended to limit in any way the definition and/or meaning of the term "computer." The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in jurisdictions that require them, but this should not be taken to mean that the features in the dependent claims are mutually exclusive.

What is claimed is:

1. An ultrasound imaging probe, comprising:
a backing layer;
an acoustic stack, including:

an interconnect coupled to the backing layer;
a transducer array electrically coupled interconnect and including at least one transducer element with a transducing surface; and
at least one matching layer with a first side acoustically coupled to the transducing surface and a second opposing side;
a compound lens, including:
an inner lens, including:
a planer inner side acoustically coupled to the second opposing side of the matching layer; and
a first non-flat side that is non-flat in elevation and wavy at least in azimuth; and
an outer lens, including:
an outer side configured to contact a subject or object; and
a second non-flat side that is non-flat in elevation and wavy at least in azimuth,
wherein the first non-flat side of the inner lens is acoustically coupled to the second non-flat side of the outer lens.

2. The ultrasound imaging probe of claim 1, wherein a first wavy pattern of the first non-flat side of the inner lens in azimuth is sinusoidal, a second wavy pattern of the second wavy side of the second non-flat side of the outer lens in azimuth is sinusoidal, and the first wavy sinusoidal pattern and the second wavy sinusoidal pattern are complementary patterns.

3. The ultrasound imaging probe of claim 1, wherein a first wavy pattern of the first non-flat side of the inner lens in azimuth is triangular, a second wavy pattern of the second wavy side of the second non-flat side of the outer lens in azimuth is triangular, and the first wavy sinusoidal pattern and the second wavy sinusoidal pattern are complementary patterns.

4. The ultrasound imaging probe of claim 1, wherein a first wavy pattern of the first non-flat side of the inner lens in azimuth is sawtooth, a second wavy pattern of the second wavy side of the second non-flat side of the outer lens in azimuth is sawtooth, and the first wavy sinusoidal pattern and the second wavy sinusoidal pattern are complementary patterns.

5. The ultrasound imaging probe of claim 1, wherein a first wavy pattern of the first non-flat side of the inner lens in azimuth is a square wave, a second wavy pattern of the second wavy side of the second non-flat side of the outer lens in azimuth is a square wave, and the first wavy sinusoidal pattern and the second wavy sinusoidal pattern are complementary patterns.

6. The ultrasound imaging probe of claim 1, wherein at least one of a first height of first waves in a first wavy pattern of the first non-flat side of the inner lens in azimuth and a second height of second waves in a second wavy pattern of the second non-flat side of the outer lens is a half wavelength.

7. The ultrasound imaging probe of claim 1, wherein at least one of a first pitch of first waves in a first wavy pattern of the first non-flat side of the inner lens in azimuth and a second pitch of second waves in a second wavy pattern of the second non-flat side of the outer lens is a half wavelength.

8. The ultrasound imaging probe of claim 1, wherein the outer lens includes a polymethylpentene.

9. The ultrasound imaging probe of claim 1, wherein the inner lens includes at least one of a polyurethane and a room-temperature-vulcanization (RTV) silicone.

10. The ultrasound imaging probe of claim 1, wherein the compound lens has a fixed depth focus in elevation.

11. The ultrasound imaging probe of claim 1, wherein a wavy interface between the first non-flat side of the inner lens in azimuth and the second non-flat side of the outer lens in azimuth is configured to trap shear waves.

12. The ultrasound imaging probe of claim 1, wherein a wavy interface between the first non-flat side of the inner lens in azimuth and the second non-flat side of the outer lens in azimuth is configured to produce destructive shear waves.

13. An ultrasound imaging system, comprising:
an ultrasound imaging probe, including:
a backing layer;
an acoustic stack, including:
an interconnect coupled to the backing layer;
a transducer array electrically coupled interconnect and including at least one transducer element with a transducing surface; and
at least one matching layer with a first side acoustically coupled to the transducing surface and a second opposing side;
a compound lens, including:
an inner lens, including:
a planer inner side acoustically coupled to the second opposing side of the matching layer; and
a first non-flat side that is non-flat in elevation and wavy in azimuth; and
an outer lens, including:
an outer side configured to contact a subject or object; and
a second non-flat side that is non-flat in elevation and wavy in azimuth,
wherein the first non-flat side of the inner lens is acoustically coupled to the second non-flat side of the outer lens; and
a console, including:
transmit circuitry that conveys an excitation pulse to the transducer array;
receive circuitry that receives a signal indicative of an ultrasound echo from the transducer array; and a beamformer that processes the received signal, generating ultrasound image data.

14. The ultrasound imaging system of claim 13, wherein the outer lens includes a polymethylpentene and the inner lens includes at least one of a polyurethane and a room-temperature-vulcanization (RTV) silicone.

15. The ultrasound imaging system of claim 14, wherein a wavy interface between the inner lens and the outer lens in azimuth is configured to at least one of trap shear waves and produce destructive shear waves.

16. The ultrasound imaging system of claim 15, wherein a height of waves in a pattern of the first and second lenses is a half wavelength, and a pitch of the waves in the pattern of the first and second lenses is a half wavelength.

17. A method, comprising:
transmitting an ultrasound pressure wave in a compound lens of an ultrasound imaging probe,
wherein the compound lens includes an inner lens with a first wavy surface in azimuth and an outer lens with a second wavy surface in azimuth, and the first wavy surface is coupled to the second wavy surface;
receiving an echo signal with the ultrasound imaging probe;
beamforming the echo signal to create an image; and
displaying the image.

18. The method of claim 17, further including:
creating a shear pressure wave resonator at an interface between the first wavy surface coupled to the second wavy surface.

19. The method of claim 17, further including:
producing destructive shear pressure waves at an interface between the first wavy surface coupled to the second wavy surface.

20. The method of claim 17, further including:
producing destructive shear pressure waves at an interface between the first wavy surface coupled to the second wavy surface.

* * * * *